United States Patent [19]
Baltz et al.

[11] Patent Number: 5,821,097
[45] Date of Patent: Oct. 13, 1998

[54] GLYCOSYLTRANSFERASE GENE GTFC FROM *AMYCOLATOPSIS ORIENTALIS*

[75] Inventors: Richard H. Baltz; Patricia J. Solenberg, both of Indianapolis, Ind.

[73] Assignee: Eli Lilly and Company, Indianapolis, Ind.

[21] Appl. No.: 924,254

[22] Filed: Sep. 5, 1997

Related U.S. Application Data

[60] Provisional application No. 60/026,029 Sep. 13, 1996.
[51] Int. Cl.$^6$ .............................. C12N 9/10; C12N 15/00; C12N 1/20; C07H 21/04
[52] U.S. Cl. ................... 435/193; 435/320.1; 435/252.3; 435/254.11; 435/325; 536/23.2
[58] Field of Search ................................ 435/193, 320.1, 435/252.3, 254.11, 325; 536/23.2

[56] References Cited

PUBLICATIONS

S. K. Chung, et al. "Biosynthetic Studies f Aridicin Antibiotics: Microbial Transformations and Glycosylations by Protoplasts." *Journal of Antibiotics* 39(5):652–659 (May 1986).

M. J. Zmijewski, Jr., and B. Briggs. "Biosynthesis of vancomycin: identification of TDP–glucose: aglycosyl–vancomycin glucosyltransferase from *Amycolatopsis orientalis*." *FEMS Microbiology Letters* 5:129–134 (1989).

M. J. Zmijewski, Jr., and J. T. Fayerman. *Genetic and Biochemistry of Antibiotic Production* Ed. L.C. Vining and C. Stuttard. Butterworth Heinemann, Boston. Chapter 18: "Glycopeptide Antibiotics." pp. 71–83 (1995).

*Primary Examiner*—Rebecca E. Prouty
*Assistant Examiner*—Lisa J. Hobbs
*Attorney, Agent, or Firm*—Thomas D. Webster; David E. Boone

[57] ABSTRACT

The invention provides isolated nucleic acid compounds encoding the glycosyltransferase protein GtfC of *Amycolatopsis orientalis*. Also provided are vectors carrying the gtfC gene, transformed heterologous host cells for expressing the GtfC protein, and methods for producing glycopeptide compounds using the cloned gtfC gene.

10 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
       ( A ) LENGTH: 1227 base pairs
       ( B ) TYPE: nucleic acid
       ( C ) STRANDEDNESS: single
       ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
       ( A ) NAME/KEY: CDS
       ( B ) LOCATION: 1..1227

( x i ) SEQUENCE DESCRIPTION: SEQ ID NO:1:

```
ATG CGT GTG TTG TTG TCG ACG GCT GGC AGC CGC GGA GAC GTC GAA CCG       48
Met Arg Val Leu Leu Ser Thr Ala Gly Ser Arg Gly Asp Val Glu Pro
 1               5                  10                  15

CTG GTG GCA TTG GCG GTT CGG CTG CAG GGG CTC GGC GTG GAG GCA CGG       96
Leu Val Ala Leu Ala Val Arg Leu Gln Gly Leu Gly Val Glu Ala Arg
            20                  25                  30

ATG TGC GCA TCG CCG GCC TCC GCG GAG CGG CTG GCC GAG GTA GGT GTG      144
Met Cys Ala Ser Pro Ala Ser Ala Glu Arg Leu Ala Glu Val Gly Val
        35                  40                  45

CCG CAC GTG CCG GTC GGC CTG CAG CTG GAG GGC ATG CTG TTG CAG GAG      192
Pro His Val Pro Val Gly Leu Gln Leu Glu Gly Met Leu Leu Gln Glu
    50                  55                  60

GGG ATG CCG CCG CCG TCG CCC GAG GAG GAG CGC CGG CTC GCG GCC AAG      240
Gly Met Pro Pro Pro Ser Pro Glu Glu Glu Arg Arg Leu Ala Ala Lys
 65                  70                  75                  80

GCG ATC GAC ATG CAG TTC GAC GAG GTC CCC GCG GCT GCC GAA GGG TGT      288
Ala Ile Asp Met Gln Phe Asp Glu Val Pro Ala Ala Ala Glu Gly Cys
                85                  90                  95

GCC GCG GTG GTG GCG GCC GGC GAG CTG GCC GCC GCG GCC GCC GTG CGG      336
Ala Ala Val Val Ala Ala Gly Glu Leu Ala Ala Ala Ala Ala Val Arg
            100                 105                 110

TCG GTG GCC GAG ATG CTG GGC ATT CCC TAC TTC TAC GCC GCC TAC AGT      384
Ser Val Ala Glu Met Leu Gly Ile Pro Tyr Phe Tyr Ala Ala Tyr Ser
        115                 120                 125

CCG AAC TAT CTG CCG TCG CCG CAC CAC GCG CCG CCC GAG GAC GAG CGG      432
Pro Asn Tyr Leu Pro Ser Pro His His Ala Pro Pro Glu Asp Glu Arg
    130                 135                 140
```

| ACC | ACG | CCG | GGC | GTG | ACC | GAC | AAC | AAG | GTG | CTG | TGG | GAC | GAG | CGT | GGC | 480 |
|---|---|---|---|---|---|---|---|---|---|---|---|---|---|---|---|---|
| Thr | Thr | Pro | Gly | Val | Thr | Asp | Asn | Lys | Val | Leu | Trp | Asp | Glu | Arg | Gly | |
| 145 | | | | 150 | | | | | 155 | | | | | | 160 | |
| CAG | CGT | TTT | GCC | AAG | CGG | TAC | GGG | GAC | ACG | CTC | AAC | AGC | AGG | CGG | GCC | 528 |
| Gln | Arg | Phe | Ala | Lys | Arg | Tyr | Gly | Asp | Thr | Leu | Asn | Ser | Arg | Arg | Ala | |
| | | | | 165 | | | | | 170 | | | | | 175 | | |
| TCG | GTC | GGC | CTG | CCA | CCG | GTT | GAG | GAC | GTC | TTC | GGC | TAC | GGC | TAC | TCC | 576 |
| Ser | Val | Gly | Leu | Pro | Pro | Val | Glu | Asp | Val | Phe | Gly | Tyr | Gly | Tyr | Ser | |
| | | | 180 | | | | | 185 | | | | | 190 | | | |
| GAG | CGG | CCC | TGG | CTG | GCG | ACG | GAC | CCG | ATC | CTG | GCC | CCG | CTG | CCG | CCG | 624 |
| Glu | Arg | Pro | Trp | Leu | Ala | Thr | Asp | Pro | Ile | Leu | Ala | Pro | Leu | Pro | Pro | |
| | | 195 | | | | | 200 | | | | | 205 | | | | |
| GAT | TTC | GAC | GCC | GTG | CAG | ACC | GGT | ACG | TGG | ATC | CTG | CCG | GAC | GAA | CGG | 672 |
| Asp | Phe | Asp | Ala | Val | Gln | Thr | Gly | Thr | Trp | Ile | Leu | Pro | Asp | Glu | Arg | |
| 210 | | | | | 215 | | | | | 220 | | | | | | |
| CCG | CTT | TCC | GCG | GAG | CTG | GAG | GCG | TTT | CTG | GCT | GCC | GGG | TCA | CCG | CCG | 720 |
| Pro | Leu | Ser | Ala | Glu | Leu | Glu | Ala | Phe | Leu | Ala | Ala | Gly | Ser | Pro | Pro | |
| 225 | | | | | 230 | | | | | 235 | | | | | 240 | |
| GTG | TAC | CTG | GGG | TTC | GGC | AGC | GCG | TCC | GGA | CCT | GGC | ATC | GAT | GAC | GCC | 768 |
| Val | Tyr | Leu | Gly | Phe | Gly | Ser | Ala | Ser | Gly | Pro | Gly | Ile | Asp | Asp | Ala | |
| | | | | 245 | | | | | 250 | | | | | 255 | | |
| GCG | AGG | GTG | GCC | ATC | GAG | GCG | ATC | CGT | GCC | CAT | GGC | CGC | CGG | ATC | GTC | 816 |
| Ala | Arg | Val | Ala | Ile | Glu | Ala | Ile | Arg | Ala | His | Gly | Arg | Arg | Ile | Val | |
| | | | 260 | | | | | 265 | | | | | 270 | | | |
| CTG | CTC | AGC | GGC | TGG | GCC | GAC | CTG | GTC | CGG | CCC | GAC | GAC | GGG | GCG | GAC | 864 |
| Leu | Leu | Ser | Gly | Trp | Ala | Asp | Leu | Val | Arg | Pro | Asp | Asp | Gly | Ala | Asp | |
| | | | 275 | | | | | 280 | | | | | 285 | | | |
| TGC | TTC | TCC | GTC | GAC | GAA | GTG | AAT | CTT | CAG | GTC | CTG | TTC | AGC | CGG | GCG | 912 |
| Cys | Phe | Ser | Val | Asp | Glu | Val | Asn | Leu | Gln | Val | Leu | Phe | Ser | Arg | Ala | |
| | | 290 | | | | | 295 | | | | | 300 | | | | |
| GCC | GCC | GCC | ATC | CAC | CAC | GGC | AGC | GCG | GGC | ACC | GAG | CAC | CTG | GCC | ACG | 960 |
| Ala | Ala | Ala | Ile | His | His | Gly | Ser | Ala | Gly | Thr | Glu | His | Leu | Ala | Thr | |
| 305 | | | | | 310 | | | | | 315 | | | | | 320 | |
| CTG | GCC | GGC | ATC | CCG | CAG | ATC | GTG | ATT | CCT | CGG | CAC | ACG | GAC | CAG | CCG | 1008 |
| Leu | Ala | Gly | Ile | Pro | Gln | Ile | Val | Ile | Pro | Arg | His | Thr | Asp | Gln | Pro | |
| | | | | 325 | | | | | 330 | | | | | 335 | | |
| TAC | TAC | GCC | GAA | CGA | GTG | GCT | GAC | CTG | GGT | ATC | GGC | GTG | GCA | CTC | GAG | 1056 |
| Tyr | Tyr | Ala | Glu | Arg | Val | Ala | Asp | Leu | Gly | Ile | Gly | Val | Ala | Leu | Glu | |
| | | | 340 | | | | | 345 | | | | | 350 | | | |
| GGT | CCG | GTC | CCG | ACC | TTC | GAC | GCG | ATG | TCG | GCC | GCG | GTC | GCC | ACG | GCC | 1104 |
| Gly | Pro | Val | Pro | Thr | Phe | Asp | Ala | Met | Ser | Ala | Ala | Val | Ala | Thr | Ala | |
| | | 355 | | | | | 360 | | | | | 365 | | | | |
| CTT | GCC | CCG | GAA | ACC | CGC | GCG | CGT | GCG | ACG | GCC | GTG | GCA | GGC | ACG | ATC | 1152 |
| Leu | Ala | Pro | Glu | Thr | Arg | Ala | Arg | Ala | Thr | Ala | Val | Ala | Gly | Thr | Ile | |
| | 370 | | | | | 375 | | | | | 380 | | | | | |
| CGC | ACC | GAC | GGG | GCA | GCG | GTG | GCC | GCG | CGG | TTG | CTG | CTC | GAC | GCG | GTC | 1200 |
| Arg | Thr | Asp | Gly | Ala | Ala | Val | Ala | Ala | Arg | Leu | Leu | Leu | Asp | Ala | Val | |
| 385 | | | | | 390 | | | | | 395 | | | | | 400 | |
| AGC | CGG | GAA | AAG | TCG | GCT | GTT | CTC | GCG | | | | | | | | 1227 |
| Ser | Arg | Glu | Lys | Ser | Ala | Val | Leu | Ala | | | | | | | | |
| | | | | 405 | | | | | | | | | | | | |

( 2 ) INFORMATION FOR SEQ ID NO:2:

( i ) SEQUENCE CHARACTERISTICS:
        ( A ) LENGTH: 409 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Arg Val Leu Leu Ser Thr Ala Gly Ser Arg Gly Asp Val Glu Pro
 1               5                  10                  15
Leu Val Ala Leu Ala Val Arg Leu Gln Gly Leu Gly Val Glu Ala Arg
              20                  25                  30
Met Cys Ala Ser Pro Ala Ser Ala Glu Arg Leu Ala Val Gly Val
              35                  40                  45
Pro His Val Pro Val Gly Leu Gln Leu Glu Gly Met Leu Leu Gln Glu
         50                  55                  60
Gly Met Pro Pro Pro Ser Pro Glu Glu Glu Arg Arg Leu Ala Ala Lys
 65                  70                  75                  80
Ala Ile Asp Met Gln Phe Asp Glu Val Pro Ala Ala Glu Gly Cys
                  85                  90                  95
Ala Ala Val Val Ala Ala Gly Glu Leu Ala Ala Ala Ala Val Arg
             100                 105                 110
Ser Val Ala Glu Met Leu Gly Ile Pro Tyr Phe Tyr Ala Ala Tyr Ser
             115                 120                 125
Pro Asn Tyr Leu Pro Ser Pro His His Ala Pro Pro Glu Asp Glu Arg
         130                 135                 140
Thr Thr Pro Gly Val Thr Asp Asn Lys Val Leu Trp Asp Glu Arg Gly
145                 150                 155                 160
Gln Arg Phe Ala Lys Arg Tyr Gly Asp Thr Leu Asn Ser Arg Arg Ala
                 165                 170                 175
Ser Val Gly Leu Pro Pro Val Glu Asp Val Phe Gly Tyr Gly Tyr Ser
             180                 185                 190
Glu Arg Pro Trp Leu Ala Thr Asp Pro Ile Leu Ala Pro Leu Pro Pro
         195                 200                 205
Asp Phe Asp Ala Val Gln Thr Gly Thr Trp Ile Leu Pro Asp Glu Arg
         210                 215                 220
Pro Leu Ser Ala Glu Leu Glu Ala Phe Leu Ala Ala Gly Ser Pro Pro
225                 230                 235                 240
Val Tyr Leu Gly Phe Gly Ser Ala Ser Gly Pro Gly Ile Asp Asp Ala
                 245                 250                 255
Ala Arg Val Ala Ile Glu Ala Ile Arg Ala His Gly Arg Arg Ile Val
             260                 265                 270
Leu Leu Ser Gly Trp Ala Asp Leu Val Arg Pro Asp Asp Gly Ala Asp
         275                 280                 285
Cys Phe Ser Val Asp Glu Val Asn Leu Gln Val Leu Phe Ser Arg Ala
     290                 295                 300
Ala Ala Ala Ile His His Gly Ser Ala Gly Thr Glu His Leu Ala Thr
305                 310                 315                 320
Leu Ala Gly Ile Pro Gln Ile Val Ile Pro Arg His Thr Asp Gln Pro
                 325                 330                 335
Tyr Tyr Ala Glu Arg Val Ala Asp Leu Gly Ile Gly Val Ala Leu Glu
             340                 345                 350
Gly Pro Val Pro Thr Phe Asp Ala Met Ser Ala Ala Val Ala Thr Ala
         355                 360                 365
Leu Ala Pro Glu Thr Arg Ala Arg Ala Thr Ala Val Ala Gly Thr Ile
         370                 375                 380
Arg Thr Asp Gly Ala Ala Val Ala Ala Arg Leu Leu Leu Asp Ala Val
385                 390                 395                 400
Ser Arg Glu Lys Ser Ala Val Leu Ala
                 405
```

( 2 ) INFORMATION FOR SEQ ID NO:3:

(i) SEQUENCE CHARACTERISTICS:
  (A) LENGTH: 1227 base pairs
  (B) TYPE: nucleic acid
  (C) STRANDEDNESS: single
  (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:3:

| | | | | | | |
|---|---|---|---|---|---|---|
| AUGCGUGUGU | UGUUGUCGAC | GGCUGGCAGC | CGCGGAGACG | UCGAACCGCU | GGUGGCAUUG | 60 |
| GCGGUUCGGC | UGCAGGGGCU | CGGCGUGGAG | GCACGGAUGU | GCGCAUCGCC | GGCCUCCGCG | 120 |
| GAGCGGCUGG | CCGAGGUAGG | UGUGCCGCAC | GUGCCGGUCG | GCCUGCAGCU | GGAGGGCAUG | 180 |
| CUGUUGCAGG | AGGGGAUGCC | GCCGCCGUCG | CCCGAGGAGG | AGCGCCGGCU | CGCGGCCAAG | 240 |
| GCGAUCGACA | UGCAGUUCGA | CGAGGUCCCC | GCGGCUGCCG | AAGGGUGUGC | CGCGGUGGUG | 300 |
| GCGGCCGGCG | AGCUGGCCGC | CGCGGCCGCC | GUGCGGUCGG | UGGCCGAGAU | GCUGGGCAUU | 360 |
| CCCUACUUCU | ACGCCGCCUA | CAGUCCGAAC | UAUCUGCCGU | CGCCGCACCA | CGCGCCGCCC | 420 |
| GAGGACGAGC | GGACCACGCC | GGGCGUGACC | GACAACAAGG | UGCUGUGGGA | CGAGCGUGGC | 480 |
| CAGCGUUUUG | CCAAGCGGUA | CGGGGACACG | CUCAACAGCA | GGCGGGCCUC | GGUCGGCCUG | 540 |
| CCACCGGUUG | AGGACGUCUU | CGGCUACGGC | UACUCCGAGC | GGCCCUGGCU | GGCGACGGAC | 600 |
| CCGAUCCUGG | CCCCGCUGCC | GCCGGAUUUC | GACGCCGUGC | AGACCGGUAC | GUGGAUCCUG | 660 |
| CCGGACGAAC | GGCCGCUUUC | CGCGGAGCUG | GAGGCGUUUC | UGGCUGCCGG | GUCACCGCCG | 720 |
| GUGUACCUGG | GGUUCGGCAG | CGCGUCCGGA | CCUGGCAUCG | AUGACGCCGC | GAGGGUGGCC | 780 |
| AUCGAGGCGA | UCCGUGCCCA | UGGCCGCCGG | AUCGUCCUGC | UCAGCGGCUG | GGCCGACCUG | 840 |
| GUCCGGCCCG | ACGACGGGGC | GGACUGCUUC | UCCGUCGACG | AAGUGAAUCU | UCAGGUCCUG | 900 |
| UUCAGCCGGG | CGGCCGCCGC | CAUCCACCAC | GGCAGCGCGG | GCACCGAGCA | CCUGGCCACG | 960 |
| CUGGCCGGCA | UCCCGCAGAU | CGUGAUUCCU | CGGCACACGG | ACCAGCCGUA | CUACGCCGAA | 1020 |
| CGAGUGGCUG | ACCUGGGUAU | CGGCGUGGCA | CUCGAGGGUC | CGGUCCCGAC | CUUCGACGCG | 1080 |
| AUGUCGGCCG | CGGUCGCCAC | GGCCCUUGCC | CCGGAAACCC | GCGCGCGUGC | GACGGCCGUG | 1140 |
| GCAGGCACGA | UCCGCACCGA | CGGGGCAGCG | GUGGCCGCGC | GGUUGCUGCU | CGACGCGGUC | 1200 |
| AGCCGGGAAA | AGUCGGCUGU | UCUCGCG | | | | 1227 |

GLYCOSYLTRANSFERASE GENE GTFC FROM *AMYCOLATOPSIS ORIENTALIS*

This application claims the benefit under Title 35, United States Code, §119(e) of United States provisional patent 60/026,029 filed Sep. 13, 1996.

BACKGROUND OF THE INVENTION

This invention relates to recombinant DNA technology. In particular the invention pertains to the cloning of glycosyltransferase gene gtfC from *Amycolatopsis orientalis,* the use of the cloned gene to express and purify the encoded enzyme, and the use of the cloned enzyme in the production of glycopeptide compounds.

The use of antibiotic compounds has had a profound impact on the practice of medicine in the United States and around the world. Two highly effective antibiotic compounds of the glycopeptide class, vancomycin and teichoplanin, have been approved for use in humans.

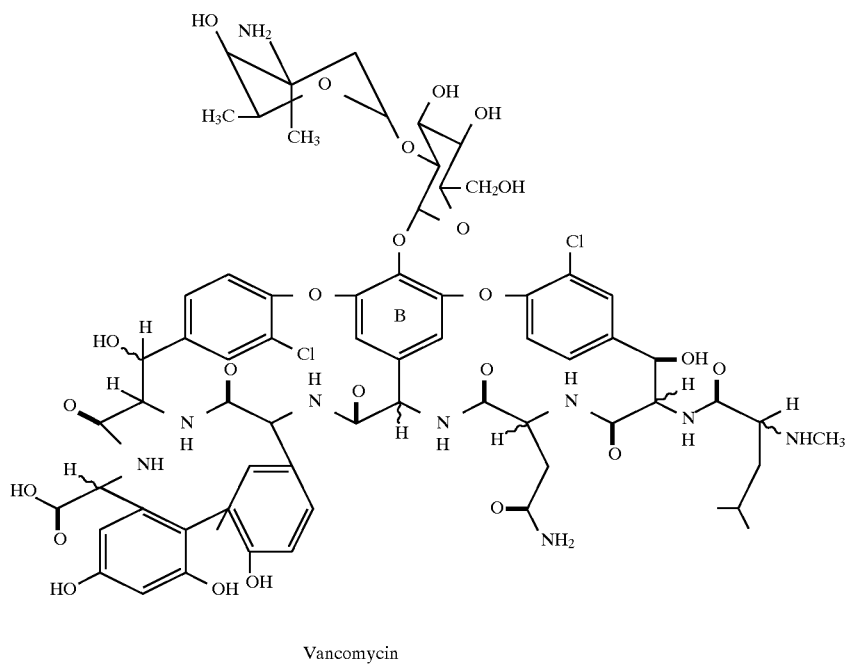

Vancomycin

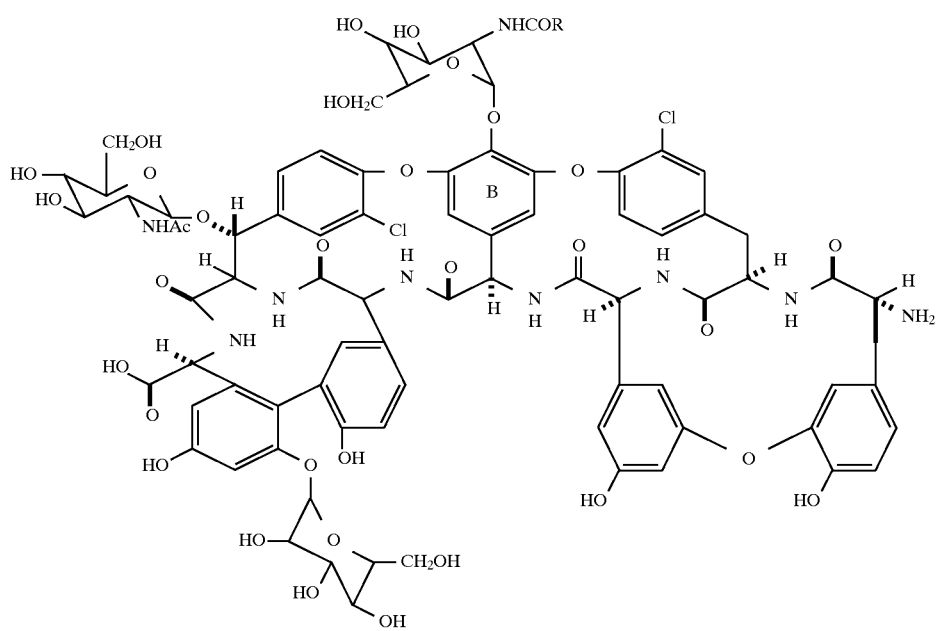

Teicoplanin: R = 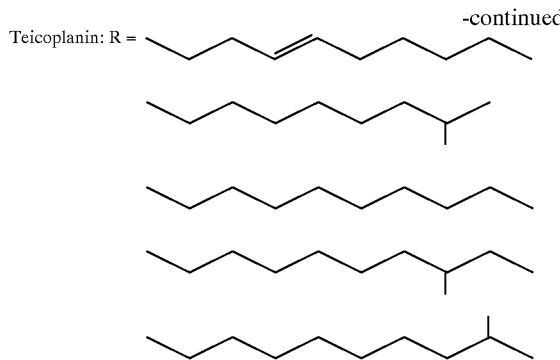

The glycopeptide antibiotics comprise natural and semi-synthetic compounds of highly functionalized linear heptapeptides having a core structure composed of either seven modified or unusual aromatic amino acids, or a mix of aromatic and aliphatic amino acids. Natural glycopeptide compounds have been found in a variety of bacterial genera including Streptomyces, Actinoplanes, Nocardia, Amycolatopsis, Kibdelosporangia, and Pseudonocardia. M. Zmijewski and J. Fayerman. "Glycopeptide Antibiotics," In *Genetics and Biochemistry of Antibiotic Production,* Chap. 18. Ed. L. C. Vining and C. Studtard. Publ. Butterworth Heinemann, Boston (1995). Generally, glycopeptide compounds are differentiated by the placement of sugar substituents on the peptide core. In some instances differentiation arises from the positioning of fatty acid moieties on the sugar substituents. Research has shown that the sugar moieties attached to the core have an effect on the biological activity of glycopeptide molecules.

At present, investigations into glycosylation of glycopeptides and glycopeptide cores are limited to preliminary observations on crude cellular extracts of bacterial strains that produce glycopeptide compounds. These experiments have demonstrated that the glycosylation reaction appears to involve one or more enzymatic activities which attach sugar residues onto a glycopeptide core. One study, for example, demonstrated a glycosylating activity in a crude cellular extract of a vancomycin-producing strain of *Amycolatopsis orientalis*. M. Zmijewski & B. Briggs. "Biosynthesis of vancomycin: identification of TDP-glucose:aglycosylvancomycin glucosyltransferase from *Amycolatopsis orientalis*" FEMS Microbiol. Lett. 59, 129–134 (1989).

The glycosylation of glycopeptide compounds, intrinsically interesting from a scientific point of view, presents a number of practical considerations that warrant continued study of this subject. Recently, a number of glycopeptide resistant strains of pathogenic organisms have been encountered within the clinical environment. This trend toward diminished efficacy of glycopeptide compounds is alarming because of a similar phenomenon in the case of β-lactam antibiotics. It is clear that the rise in antibiotic resistance has occured by a plurality of molecular mechanisms and that resistant organisms possess a diverse repertoire for counter-acting the otherwise lethal effect of antibiotic compounds.

In light of the trend toward greater resistance, and in view of the absence of effective alternative treatments, there exists a pressing need to develop new antibiotic compounds. A useful strategy toward this end involves derivitizing presently available glycopeptide compounds by engineering in defined ways the placement and configuration of sugar moieties on the glycopeptide core structure. Achieving molecular rearrangements and substitutions on glycopeptide compounds by chemical means is difficult if not impossible in most cases. By contrast to chemical procedures, enzymatic methods, if available, would provide an effective means to engineer specific modifications onto the glycopeptide core.

The challenge to provide an enzymatic means for modifying glycopeptide core molecules has been met by the present invention. Described herein are gtfC genes isolated from *Amycolatopsis orientalis* which encode glycosyltransferase enzyme GtfC. This enzyme adds epivancosamine onto glycopeptides of the vancomycin class.

BRIEF SUMMARY

The present invention is designed to meet the aforementioned need and provides, inter alia, the isolated gtfC gene and other nucleic acid molecules that encode the GtfC gene product from *Amycolatopsis orientalis* A82846. The invention also provides the GtfC protein product of the *Amycolatopsis orientalis* gtfC gene, in substantially purified form.

Having the cloned gtfC gene of *Amycolatopsis orientalis* enables the production of recombinant GtfC protein from which can be made derivatives of glycopeptide compounds.

In one embodiment the present invention relates to an isolated DNA molecule encoding GtfC protein, said DNA molecule comprising the nucleotide sequence identified as SEQ ID NO. 1:

ATGCGTGTGT TGTTGTCGAC GGCTGGCAGC CGCG-
GAGACG TCGAACCGCT GGTGGCATTG 60

GCGGTTCGGC TGCAGGGGCT CGGCGTGGAG GCACG-
GATGT GCGCATCGCC GGCCTCCGCG 120

GAGCGGCTGG CCGAGGTAGG TGTGCCGCAC GTGCCG-
GTCG GCCTGCAGCT GGAGGGCATG 180

CTGTTGCAGG AGGGGATGCC GCCGCCGTCG CCCGAG-
GAGG AGCGCCGGCT CGCGGCCAAG 240

GCGATCGACA TGCAGTTCGA CGAGGTCCCC GCGGCT-
GCCG AAGGGTGTGC CGCGGTGGTG 300

GCGGCCGGCG AGCTGGCCGC CGCGGCCGCC GTGCG-
GTCGG TGGCCGAGAT GCTGGGCATT 360

CCCTACTTCT ACGCCGCCTA CAGTCCGAAC TATCTGCCGT
CGCCGCACCA CGCGCCGCCC 420

GAGGACGAGC GGACCACGCC GGGCGTGACC GACAA-
CAAGG TGCTGTGGGA CGAGCGTGGC 480

CAGCGTTTTG CCAAGCGGTA CGGGGACACG CTCAA-
CAGCA GGCGGGCCTC GGTCGGCCTG 540

```
CCACCGGTTG AGGACGTCTT CGGCTACGGC TACTC-
    CGAGC GGCCCTGGCT GGCGACGGAC 600

CCGATCCTGG CCCCGCTGCC GCCGGATTTC GACGC-
    CGTGC AGACCGGTAC GTGGATCCTG 660

CCGGACGAAC GGCCGCTTTC CGCGGAGCTG GAG-
    GCGTTTC TGGCTGCCGG GTCACCGCCG 720

GTGTACCTGG GGTTCGGCAG CGCGTCCGGA CCTG-
    GCATCG ATGACGCCGC GAGGGTGGCC 780

ATCGAGGCGA TCCGTGCCCA TGGCCGCCGG ATCGTC-
    CTGC TCAGCGGCTG GGCCGACCTG 840

GTCCGGCCCG ACGACGGGGC GGACTGCTTC TCCGTC-
    GACG AAGTGAATCT TCAGGTCCTG 900

TTCAGCCGGG CGGCCGCCGC CATCCACCAC
    GGCAGCGCGG GCACCGAGCA CCTGGCCACG 960

CTGGCCGGCA TCCCGCAGAT CGTGATTCCT CGGCA-
    CACGG ACCAGCCGTA CTACGCCGAA 1020

CGAGTGGCTG ACCTGGGTAT CGGCGTGGCA CTC-
    GAGGGTC CGGTCCCGAC CTTCGACGCG 1080

ATGTCGGCCG CGGTCGCCAC GGCCCTTGCC CCG-
    GAAACCC GCGCGCGTGC GACGGCCGTG 1140

GCAGGCACGA TCCGCACCGA CGGGGCAGCG GTGGC-
    CGCGC GGTTGCTGCT CGACGCGGTC 1200

AGCCGGGAAA AGTCGGCTGT TCTCGCG 1227
```

In another embodiment the present invention relates to a glycosyltransferase protein molecule, encoded by SEQ ID NO:1 wherein said glycosyltransferase protein molecule comprises the sequence identified as SEQ ID NO. 2.

In a further embodiment the present invention relates to a ribonucleic acid molecule encoding GtfC protein, said ribonucleic acid molecule comprising the sequence identified as SEQ ID NO. 3:

In yet another embodiment, the present invention relates to a recombinant DNA vector which incorporates the *Amycolatopsis orientalis* gtfC gene in operable linkage to gene expression sequences enabling the gtfC gene to be transcribed and translated in a host cell.

In still another embodiment the present invention relates to homologous or heterologous host cells which have been transformed or transfected with the cloned gtfC gene of *Amycolatopsis orientalis* such that the gtfC gene is expressed in the host cell.

In still another embodiment the present invention relates to a method for producing glycopeptide compounds in vitro wherein recombinantly produced GtfC protein is utilized to add one or more sugar moieties onto a glycopeptide core.

In a further embodiment the present invention relates to a composition comprising a vancomycin core having attached thereto at least one epivancosamine moiety, said composition produced by the action of a recombinant GtfC protein.

Definitions

"AGV" denotes aglycosylvancomycin which comprises a vancomycin core having a free hydroxl group on the B ring in place of the disaccharide moiety.

"DVV" denotes desvancosaminyl vancomycin in which a glucose residue is attached onto AGV at the free hydroxl position of the B ring.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

The term "fusion protein" denotes a hybrid protein molecule not found in nature comprising a translational fusion or enzymatic fusion in which two or more different proteins or fragments thereof are covalently linked on a single polypeptide chain.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

The term "glycopeptide" refers to a functionalized linear heptapeptide compound of natural or semi-synthetic origin, said compound having a core structure.

"Glycopeptide core" or "core" or "core compound" interchangeably denote the progenitor structure of all glycopeptide compounds, comprising either 7 modified or unusual aromatic amino acids, or a mix of aromatic and aliphatic amino acids.

"Vancomycin glycopeptide" refers to any or all of the following: AGV, DVV, vancomycin.

"Glycosylating substrate" refers to a compound which functions as a donor of a sugar moiety in an enzymatic glycosylation reaction, for example, uridine diphosphate-D-glucose.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which hybridizes with another nucleic acid compound.

The term "hybridization" as used herein refers to a process in which two or more strands of nucleic acid join through base pairing with complementary strands. "Selective hybridization" refers to hybridization under conditions of high stringency. The degree of hybridization between nucleic acid molecules varies with the degree of complementarity, the stringency of the hybridization conditions, and the length of the strands.

The term "stringency" refers to a set of hybridization conditions, for example temperature and salt concentration, which may be varied to achieve "high stringency" or "low stringency" conditions, thereby varying the degree of hybridization of one nucleic acid molecule with another nucleic acid molecule. High stringency conditions disfavor non-homologous basepairing.

DETAILED DESCRIPTION

The gtfC gene of *Amycolatopsis orientalis* encodes a glycosylating enzyme, GtfC. The enzyme will add epivancosamine onto a vancomycin glycopeptide or core compound. The enzyme will use TDP-epivancosamine or UDP-epivancosamine as a glycosylating substrate.

The gtfC gene of *Amycolatopsis orientalis* comprises a DNA sequence of 1227 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product identified as SEQ ID NO:2. All such substitutions are intended to be within the scope of the invention.

Gene Isolation Procedures

Those skilled in the art will recogize that the gtfC gene may be obtained by a plurality of applicable techniques including, for example, polymerase chain reaction (PCR) amplification, or de novo DNA synthesis.(See e.g., J. Sambrook et al. *Molecular Cloning*, 2d Ed. Chap. 14 (1989)).

Methods for constructing gene libraries in a suitable vector such as a plasmid or phage for propagation in procaryotic or eucaryotic cells are well known to those skilled in the art. [See e.g. J. Sambrook et al. Supra]. Suitable cloning vectors are widely available.

Skilled artisans will recognize that the gtfC gene of *Amycolatopsis orientalis* or fragment thereof could also be isolated by PCR amplification of *Amycolatopsis orientalis* genomic DNA using oligonucleotide primers targeted to any suitable region of SEQ ID NO. 1. Methods for PCR amplification are widely known in the art. See e.g. *PCR Protocols: A Guide to Method and Application,* Ed. M. Innis et al., Academic Press (1990), which hereby is incorporated by reference. The PCR amplification, which comprises genomic DNA, suitable enzymes, primers, and buffers, is conveniently carried out in a DNA Thermal Cycler (Perkin Elmer Cetus, Norwalk, Conn.). A positive PCR amplification is determined by detecting an appropriately-sized DNA fragment following agarose gel electrophoresis.

Protein Production Methods

One embodiment of the present invention relates to the substantially purified protein GtfC identified as SEQ ID NO:2 and encoded by the gtfC gene or functionally related proteins of *Amycolatopsis orientalis*.

Skilled artisans will recognize that the proteins of the present invention can be synthesized or purified by any number of suitable methods. For example, the amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and are described in a number of general texts on the subject. See, e.g., H. Dugas and C. Penney, *Bioorganic Chemistry* (1981) Springer-Verlag, New York, 54–92. For example, peptides may be synthesized by solid-phase methodology using an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double-couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celcius or below, preferably −20_C. for thirty minutes followed by thirty minutes at 0_C.

The proteins of the present invention can also be produced by recombinant DNA methods using the cloned gtfC gene of *Amycolatopsis orientalis*. Recombinant methods are preferred if a high yield is desired. Expression of the cloned gtfC gene can be carried out in a variety of suitable host cells well known to those skilled in the art. The gtfC gene is introduced into a host cell by any suitable transformation, transfection, or conjugation means, well known to those skilled in the art. While chromosomal integration of the cloned gtfC gene is within the scope of the present invention, it is preferred that the gene be cloned into a suitable extra-chromosomally maintained expression vector so that the coding region of the gtfC gene is operably linked to a constitutive or inducible promoter.

The basic steps in the recombinant production of the GtfC protein are:

a) constructing a natural, synthetic or semi-synthetic DNA encoding GtfC protein;

b) integrating said DNA into an expression vector in a manner suitable for expressing the GtfC protein, either alone or as a fusion protein;

c) transforming, transfecting, or otherwise introducting said expression vector into an appropriate eukaryotic or prokaryotic host cell to form a recombinant host cell, d) culturing said recombinant host cell under conditions that favor expression of the GtfC protein; and e) recovering and purifying the GtfC protein by any suitable means.

Expressing Recombinant GtfC Protein in Procaryotic and Eucaryotic Host Cells

In general, prokaryotes are used for cloning DNA and for constructing the vectors of the present invention. Prokaryotes are also employed in the production of the GtfC protein. For example, the *Escherichia coli* K12 strain 294 (ATCC No. 31446) is particularly useful for the expression of foreign proteins. Other strains of *E. coli,* bacilli such as

*Bacillus subtilis,* enterobacteriaceae such as *Salmonella typhimurium* or *Serratia marcescans,* various Pseudomonas species, and other bacteria, such as Streptomyces, may also be employed as host cells in the cloning and expression of the recombinant proteins of this invention.

Promoters suitable for driving the expression of gene sequences in prokaryotes include β-lactamase [e.g. vector pGX2907, ATCC 39344, contains a replicon and β-lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The protein of this invention may be synthesized by recombinant or chemical means as the amino acid sequence identified as SEQ ID NO:2, or as a fusion protein comprising the protein of interest and another protein or peptide which may be removable by enzymatic or chemical cleavage. Expression as a fusion protein may prolong the lifespan, increase the yield of the desired peptide, or provide a convenient means for purifying the protein. A variety of peptidases (e.g. enterokinase and thrombin) which cleave a polypeptide at specific sites are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes,* American Chemical Society, Washington, D.C. (1990).

In addition to prokaryotes, mammalian host cells and eukaryotic microbes such as yeast may also be used to isolate and express the genes of the present invention. The simple eucaryote *Saccharomyces cerevisiae,* is the most commonly used eukaryotic microorganism, although a number of other yeasts such as *Kluyveromyces lactis* are also suitable. For expression in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trp1 auxotrophic mutant.

Purification of Recombinantly-Produced GtfC Protein

An expression vector carrying the cloned gtfC gene of *Amycolatopsis orientalis* is transformed, transfected, or introduced by conjugation into a suitable host cell using standard methods. Suitable conjugation methods are described in P. Matsushima and R. H. Baltz, "A gene cloning system for *Streptomyces toyocaensis*" Microbiol. 142, 261–267 (1996), which hereby is incorporated by reference. Cells which contain the vector are propagated under conditions suitable for expression of the Glycosyltransferase protein. If the gtfC gene is under the control of an inducible promoter, growth media and other conditions should incorporate the appropriate inducer.

The recombinantly produced protein may be purified from cellular extracts of transformed cells by any suitable means. In a preferred protein purification method, the gtfC gene is modified at the 5' end to incorporate several histidine residues at the amino terminus of the GtfC protein product. The "histidine tag" enables a single-step protein purification method referred to as "immobilized metal ion affinity chromatography" (IMAC), essentially as described in M. C. Smith et al. "Chelating Peptide-immobilized metal-ion affinity chromatography," Chapter 12, in *Protein Purification: From Molecular Mechanisms to Large Scale Processes,* American Chemical Society, Washington, D.C. (1990), and in U.S. Pat. No. 4,569,794 both of which hereby are incorporated by reference. The IMAC method enables rapid isolation of substantially pure protein.

The gtfC gene, which comprises nucleic acid encoding SEQ ID NO:2, may also be produced using synthetic methodology. The synthesis of nucleic acids is well known in the art. See, e.g., E. L. Brown, R. Belagaje, M. J. Ryan, and H. G. Khorana, *Methods in Enzymology,* 68:109–151 (1979). The DNA segments corresponding to the gtfC gene could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach,* (1984).]

The ribonucleic acids of the present invention may be prepared using the polynucleotide synthetic methods discussed supra, or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. These RNA polymerases are highly specific and require the insertion of bacteriophage-specific sequences at the 5' end of the template to be transcribed. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for a variety of molecular biology techniques. For example, the nucleic acid compounds of the present invention may be used to hybridize to genomic DNA which has been digested with one or more restriction enzymes and separated on an electrophoretic gel. The hybridization of radiolabeled probes onto such restricted DNA, usually fixed to a membrane after electrophoresis, is well known in the art. See, e.g., J. Sambrook, supra. A compound which comprises SEQ ID NO:1, SEQ ID NO:3 or a complementary sequence of SEQ ID NO:1 or SEQ ID NO:3, or a fragment thereof, and which is at least 18 base pairs in length, and which will selectively hybridize to *Amycolatopsis orientalis* DNA or mRNA encoding gtfC, is provided. Preferably, the 18 or more base pair compound is DNA. The probes and primers of this invention can be prepared by techniques well known to those skilled in the art (See e.g. Sambrook et al. supra). In a most preferred embodiment these probes and primers are synthesized using chemical means as described above.

Another aspect of the present invention relates to recombinant DNA cloning vectors and expression vectors comprising the nucleic acids of the present invention. Many of the vectors encompassed within this invention are described above. The preferred nucleic acid vectors are those which comprise DNA. The most preferred recombinant DNA vectors comprise the isolated DNA sequence, SEQ ID NO:1. Plasmid pCZA365 is an especially preferred DNA vector of the present invention.

Choosing the most appropriate cloning vector or expression vector depends upon a number of factors including the availability of appropriate restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance markers and metabolic markers), and the desired number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they enable high level, regulatable expression of an operably linked gene. A number of inducible promoters responding to a variety of induction signals are available, for example, carbon source, metal ions, and heat. The practitioner also understands that the amount of nucleic acid or protein to be produced dictates, in part, the selection of the expression system. The addition of certain nucleotide sequences, such as a sequence encoding a signal peptide preceding the coding sequence, is useful to direct localization of the resulting polypeptide.

Host cells harboring the nucleic acids disclosed herein are also provided by the present invention. A preferred host is *E. coli* which has been transfected or transformed with a vector which comprises a nucleic acid of the present invention.

The present invention also provides a method for constructing a recombinant host cell capable of expressing SEQ ID NO:2, said method comprising transforming or otherwise introducing into a host cell a recombinant DNA vector that comprises an isolated DNA sequence which encodes SEQ ID NO:2. A preferred host cell is any strain of *E. coli* which can accomodate high level expression of a gene(s) introduced by transformation or transfection. Preferred vectors for expression are those which comprise SEQ ID NO:1. An especially preferred expression vector for use in *E. coli* is plasmid pCZA365, which comprises SEQ ID NO:1. Transformed host cells may be cultured under conditions well known to skilled artisans such that SEQ ID NO:2 is expressed, thereby producing GtfC protein in the recombinant host cell.

The instant invention provides an enzymatic method for glycosylating vancomycin glycopeptides and core compounds using the cloned *A. orientalis* gtfC gene, said method comprising the steps of:

a) expressing the cloned gtfC gene in a host cell so that GtfC enzyme is produced;
b) exposing said GtfC enzyme to a glycopeptide compound, in vitro;
c) introducing a suitable glycosylating substrate; and
d) characterizing and/or purifying the product glycopeptide by any suitable means.

The instant method can be used to enzymatically attach epivancomsamine residues to glycopeptide molecules such as, for example, members of the vancomycin glycopeptide class. The method will attach a epivancosamine onto desvancosaminyl vancomycin.

The method can be adapted to substantially purified recombinant GtfC protein, as described herein, or to a crude cellular extract isolated from a recombinant cell culture that expresses the GtfC protein by virtue of having been transformed, transfected, or otherwise imbued with the gtfC gene.

A suitable substrate for the in vitro glycosylation reaction comprises TDP-epivancosamine. This substrate can be obtained by acid-catalyzed hydrolysis of compound A82846B using any suitable method known to skilled artisans (See e.g. M. Sim et al. "Synthesis and use of glycosyl phosphites: an effective route to glycosyl phophates, sugar nucleotides, and glycosides" J. Am. Chem. Soc. 115, 2260–67 (1993)). In one method for preparation of this substrate, following acid hydrolysis of A82846B the hydrolytic products are condensed with dibenzyl N,N-diethylphosphoramidite as a phosphitylating reagent so as to generate the appropriate dibenzyl glycosyl phosphite derivative. Oxidation and deprotection, followed by reaction with thymidine 5'-monophospho-morpholidate provides the desired sugar substrate.

The following examples more fully describe the present invention. Those skilled in the art will recognize that the particular reagents, equipment, and procedures described are merely illustrative and are not intended to limit the present invention in any manner.

EXAMPLE 1

Construction of a DNA Vector for Expressing *Amycolatopsis orientalis* Gene gtfC in *Escherichia coli*

Plasmid pCZA365 is an approximately 7 kilobasepair expression vector suitable for expressing the gtfC gene at high levels in a procaryotic host, for example *E. coli*. Plasmid pCZA365 is derived from parent plasmid PET-11a (obtained from Novagen, Madison, Wis.), which contains an origin of DNA replication (ori), an ampicillin resistance gene (Amp), the T7 promoter region, and the lacI gene for repressing the lac operon.

The gtfC gene cassette inserted into pCZA365 is generated by the PCR carried out on *A. orientalis* A82846 genomic DNA using standard conditions. Primers used in the amplification reaction are complementary to the 5' and 3' ends of the gtfC gene sequence specified in SEQ ID NO: 1 and are engineered to contain NdeI and BglII restriction sites. The PCR-amplified gtfC gene sequence is digested with NdeI and BglII and ligated into pET11a, which has been digested with NdeI and BamHI.

EXAMPLE 2

Transformation of *Escherichia coli* with an Expression Plasmid Carrying the gtfC gene of *Amycolatopsis orientalis*

Plasmid pCZA365 is transformed into *E. coli* BL21(DE3) (hsdS gal λcIts857 ind1Sam7nin5lacUV5-T7gene 1) using standard methods (See e.g. Sambrook et al. Supra).

EXAMPLE 3

In Vitro Glycosylation of Desvancosaminyl Vancomycin Using Cloned gtfC Gene

Approximately 25 ml of a culture of *E. coli* BL21(DE3) cells transformed with plasmid pCZA365 is grown to an OD$_{600}$ of about 0.6. Induction of gtfC gene expression is effected by adding 1 m IPTG with shaking at room temperature for 2 to 3 hours. Thereafter, cells from about 20 ml of the induced culture are pelleted by centrifugation and resuspended in 2 ml of 50 mM Tris pH 9.0, 100 μg/ml lysozyme with incubation on ice for 10 minutes to effect cell lysis. After cell lysis the suspension is passed through a 23-gauge syringe and centrifuged at 10,000×g for 15 minutes to pellet cell debris. The resulting cell extract is used for the glycosylation reaction.

The 1 ml glycosylation reaction contained:
1 mg DVV in 50 mM Tris HCL, pH 9.0
5 mg TDP-epivancosamine
1 mg bovine serum albumin (BSA)
20 μl 1M MgCl2
20 μl 1M CaCl2
5 μl 1M dithiothreitol (DTT)
445 μl cell extract
Distilled water to 1 ml.

A control reaction contained cell extract from non-transformed BL21(DE3). After incubation overnight at 37_C. with slight shaking the reaction is filtered through a 0.45 micron filter and analyzed by HPLC.

---

We claim:

1. An isolated nucleic acid compound encoding the protein having the amino acid sequence which is SEQ ID NO 2.

2. An isolated nucleic acid compound comprising a sequence encoding the protein of SEQ ID NO:2 wherein said compound has a sequence selected from the group consisting of:

(a)

ATGCGTGTGT TGTTGTCGAC GGCTGGCAGC CGCG-
GAGACG TCGAACCGCT GGTGGCATTG 60

GCGGTTCGGC TGCAGGGGCT CGGCGTGGAG GCACG-
GATGT GCGCATCGCC GGCCTCCGCG 120

GAGCGGCTGG CCGAGGTAGG TGTGCCGCAC GTGCCG-
GTCG GCCTGCAGCT GGAGGGCATG 180

CTGTTGCAGG AGGGGATGCC GCCGCCGTCG CCCGAG-
GAGG AGCGCCGGCT CGCGGCCAAG 240

GCGATCGACA TGCAGTTCGA CGAGGTCCCC GCGGCT-
GCCG AAGGGTGTGC CGCGGTGGTG 300

GCGGCCGGCG AGCTGGCCGC CGCGGCCGCC GTGCG-
GTCGG TGGCCGAGAT GCTGGGCATT 360

CCCTACTTCT ACGCCGCCTA CAGTCCGAAC TATCTGCCGT
CGCCGCACCA CGCGCCGCCC 420

GAGGACGAGC GGACCACGCC GGGCGTGACC GACAA-
CAAGG TGCTGTGGGA CGAGCGTGGC 480

CAGCGTTTTG CCAAGCGGTA CGGGGACACG CTCAA-
CAGCA GGCGGGCCTC GGTCGGCCTG 540

CCACCGGTTG AGGACGTCTT CGGCTACGGC TACTC-
CGAGC GGCCCTGGCT GGCGACGGAC 600

CCGATCCTGG CCCCGCTGCC GCCGGATTTC GACGC-
CGTGC AGACCGGTAC GTGGATCCTG 660

```
CCGGACGAAC GGCCGCTTTC CGCGGAGCTG GAG-
    GCGTTTC TGGCTGCCGG GTCACCGCCG 720

GTGTACCTGG GGTTCGGCAG CGCGTCCGGA CCTG-
    GCATCG ATGACGCCGC GAGGGTGGCC 780

ATCGAGGCGA TCCGTGCCCA TGGCCGCCGG ATCGTC-
    CTGC TCAGCGGCTG GGCCGACCTG 840

GTCCGGCCCG ACGACGGGGC GGACTGCTTC TCCGTC-
    GACG AAGTGAATCT TCAGGTCCTG 900

TTCAGCCGGG CGGCCGCCGC CATCCACCAC
    GGCAGCGCGG GCACCGAGCA CCTGGCCACG 960

CTGGCCGGCA TCCCGCAGAT CGTGATTCCT CGGCA-
    CACGG ACCAGCCGTA CTACGCCGAA 1020

CGAGTGGCTG ACCTGGGTAT CGGCGTGGCA CTC-
    GAGGGTC CGGTCCCGAC CTTCGACGCG 1080

ATGTCGGCCG CGGTCGCCAC GGCCCTTGCC CCG-
    GAAACCC GCGCGCGTGC GACGGCCGTG 1140

GCAGGCACGA TCCGCACCGA CGGGGCAGCG GTGGC-
    CGCGC GGTTGCTGCT CGACGCGGTC 1200

AGCCGGGAAA AGTCGGCTGT TCTCGCG 1227
``` which is SEQ ID NO:1;

(b)

```
AUGCGUGUGU UGUUGUCGAC GGCUGGCAGC CGCG-
    GAGACG UCGAACCGCU GGUGGCAUUG 60

GCGGUUCGGC UGCAGGGGCU CGGCGUGGAG GCACG-
    GAUGU GCGCAUCGCC GGCCUCCGCG 120

GAGCGGCUGG CCGAGGUAGG UGUGCCGCAC GUGC-
    CCGUCG GCCUGCAGCU GGAGGGCAUG 180

CUGUUGCAGG AGGGGAUGCC GCCGCCGUCG CCCGAG-
    GAGG AGCGCCGGCU CGCGGCCAAG 240

GCGAUCGACA UGCAGUUCGA CGAGGUCCCC GCG-
    GCUGCCG AAGGGUGUGC CGCGGUGGUG 300

GCGGCCGGCG AGCUGGCCGC CGCGGCCGCC GUGCG-
    GUCGG UGGCCGAGAU GCUGGGCAUU 360

CCCUACUUCU ACGCCGCCUA CAGUCCGAAC UAUCUGC-
    CGU CGCCGCACCA CGCGCCGCCC 420

GAGGACGAGC GGACCACGCC GGGCGUGACC GACAA-
    CAAGG UGCUGUGGGA CGAGCGUGGC 480

CAGCGUUUUG CCAAGCGGUA CGGGGACACG CUCAA-
    CAGCA GGCGGGCCUC GGUCGGCCUG 540

CCACCGGUUG AGGACGUCUU CGGCUACGGC UACUC-
    CGAGC GGCCCUGGCU GGCGACGGAC 600
```

CCGAUCCUGG CCCCGCUGCC GCCGGAUUUC GACGC-
    CGUGC AGACCGGUAC GUGGAUCCUG 660

CCGGACGAAC GGCCGCUUUC CGCGGAGCUG GAGGCGU-
    UUC UGGCUGCCGG GUCACCGCCG 720

GUGUACCUGG GGUUCGGCAG CGCGUCCGGA CCUG-
    GCAUCG AUGACGCCGC GAGGGUGGCC 780

AUCGAGGCGA UCCGUGCCCA UGGCCGCCGG AUCGUC-
    CUGC UCAGCGGCUG GGCCGACCUG 840

GUCCGGCCCG ACGACGGGGC GGACUGCUUC UCCGUC-
    GACG AAGUGAAUCU UCAGGUCCUG 900

UUCAGCCGGG CGGCCGCCGC CAUCCACCAC
    GGCAGCGCGG GCACCGAGCA CCUGGCCACG 960

CUGGCCGGCA UCCCGCAGAU CGUGAUUCCU CGGCA-
    CACGG ACCAGCCGUA CUACGCCGAA 1020

CGAGUGGCUG ACCUGGGUAU CGGCGUGGCA CUC-
    GAGGGUC CGGUCCCGAC CUUCGACGCG 1080

AUGUCGGCCG CGGUCGCCAC GGCCCUUGCC CCG-
    GAAACCC GCGCGCGUGC GACGGCCGUG 1140

GCAGGCACGA UCCGCACCGA CGGGGCAGCG GUGGC-
    CGCGC GGUUGCUGCU CGACGCGGUC 1200

AGCCGGGAAA AGUCGGCUGU UCUCGCG 1227 which is SEQ ID NO:3;

(c) a nucleic acid compound complementary to (a) or (b).

3. An isolated nucleic acid compound of claim 2 wherein the sequence of said compound is SEQ ID NO:1 or a sequence complementary to SEQ ID NO:1.

4. An isolated nucleic acid compound of claim 2 wherein the sequence of said compound is SEQ ID NO:3 or a sequence complementary to SEQ ID NO:3.

5. A vector comprising an isolated nucleic acid compound of claim 2.

6. A vector, as in claim 5, wherein said isolated nucleic acid compound is DNA operably linked to a promoter sequence.

7. A host cell containing the vector of claim 5.

8. A host cell containing the vector of claim 6.

9. A method for constructing a recombinant host cell having the potential to express SEQ ID NO:2, said method comprising introducing into said host cell by any suitable means a vector of claim 6.

10. A method for expressing SEQ ID NO:2 in the recombinant host cell of claim 9, said method comprising culturing said recombinant host cell under conditions suitable for gene expression.

* * * * *